(12) United States Patent
Huang et al.

(10) Patent No.: US 9,907,763 B2
(45) Date of Patent: Mar. 6, 2018

(54) METHOD OF TREATING OR PREVENTING THE VISUAL FUNCTION LOSS BY USING 4-(PHENYLSULFANYL)BUTANE-2-ONE (4-PSB-2)

(71) Applicants: NATIONAL SUN YAT-SEN UNIVERSITY, Kaohsiung (TW); TZU-CHI UNIVERSITY, Hualien (TW)

(72) Inventors: Shun-Ping Huang, Hualien (TW); Jyh-Horng Sheu, Kaohsiung (TW); Zhi-Hong Wen, Kaohsiung (TW); Rong-Kung Tsai, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 15/299,547

(22) Filed: Oct. 21, 2016

(65) Prior Publication Data

US 2017/0304219 A1    Oct. 26, 2017

(30) Foreign Application Priority Data

Apr. 22, 2016   (TW) .............................. 105112654 A

(51) Int. Cl.
*A61K 31/10*   (2006.01)
*A61K 31/12*   (2006.01)
*A61K 9/00*    (2006.01)

(52) U.S. Cl.
CPC ................ *A61K 31/12* (2013.01); *A61K 9/00* (2013.01)

(58) Field of Classification Search
CPC ....................................................... A61K 31/12
USPC ........................................................ 514/712
See application file for complete search history.

(56) References Cited

PUBLICATIONS

Chien et al. Experimental Eye Research (2016), 143, 148-157 Available online Oct. 22, 2015.*

* cited by examiner

*Primary Examiner* — Nizal Chandrakumar
(74) *Attorney, Agent, or Firm* — Hannah M. Tien

(57) ABSTRACT

The present invention relates to a method of treating or preventing the visual function loss in optic nerve in a subject after crush injury by using 4-(Phenylsulfanyl)butane-2-one (4-PSB-2). The present invention has the ability of enhancing the protection effect of RGCs, preserving the visual function in optic nerve after crush injury, recovering the visual function loss, attenuating apoptosis in optic nerve after injury, and inhibiting the inflammatory responses in optic nerves after ON injury.

8 Claims, 7 Drawing Sheets
(4 of 7 Drawing Sheet(s) Filed in Color)

Figure 1
Figure 1A
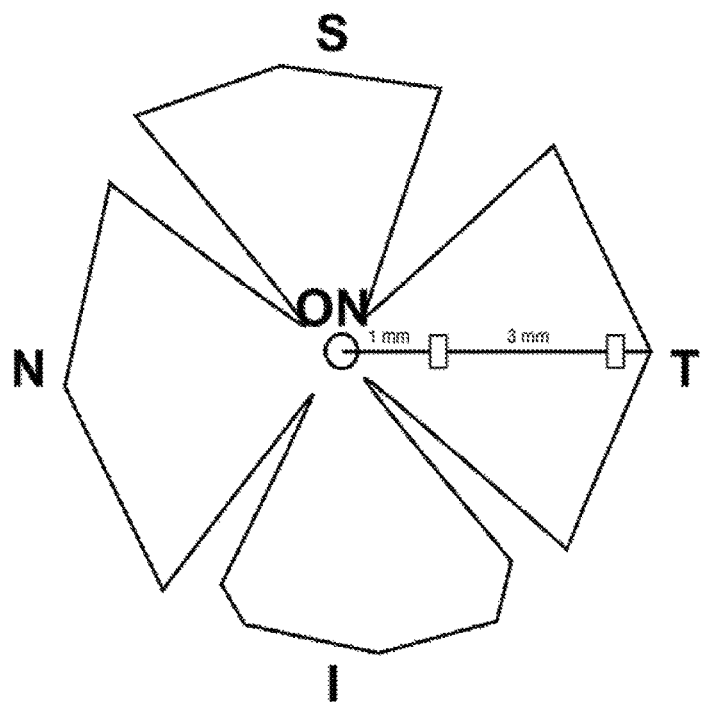
Figure 1B
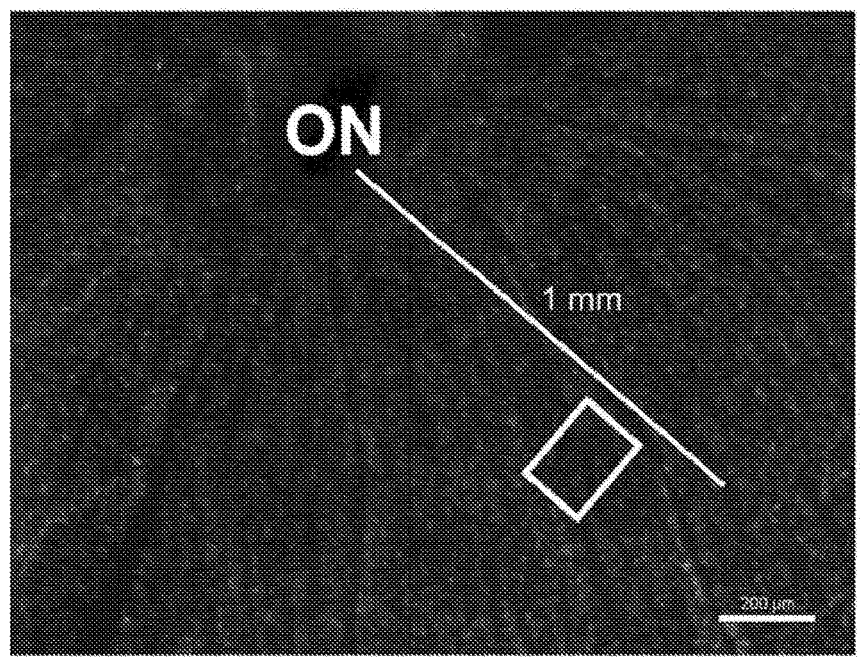

Figure 3
Figure 3A
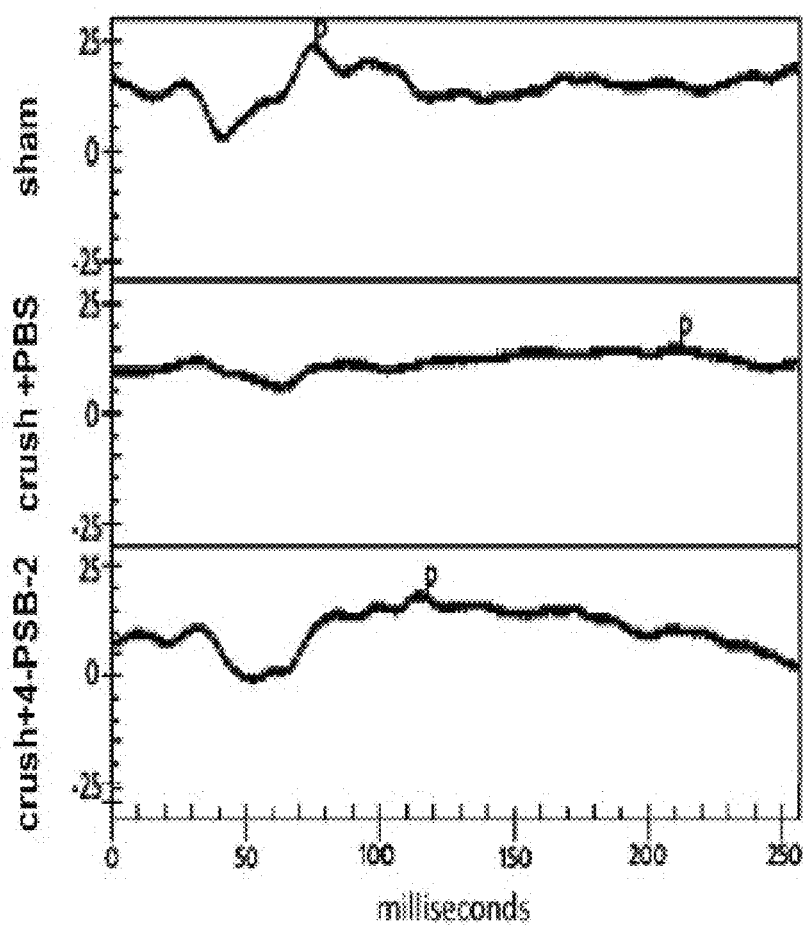
Figure 3B
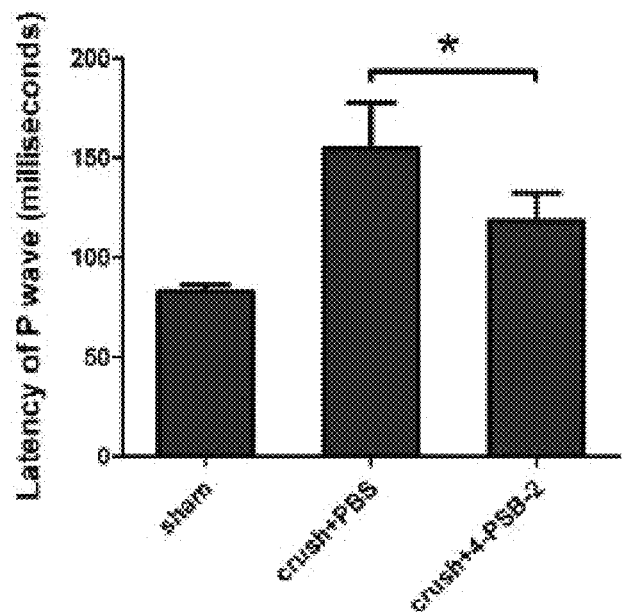

Figure 4
Figure 4A
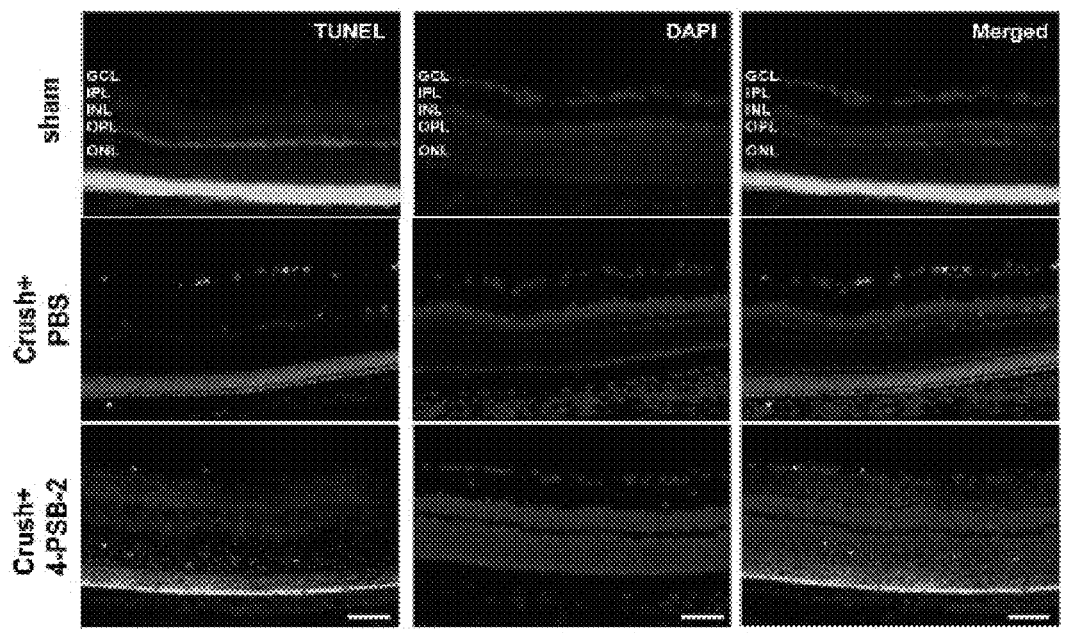
Figure 4B
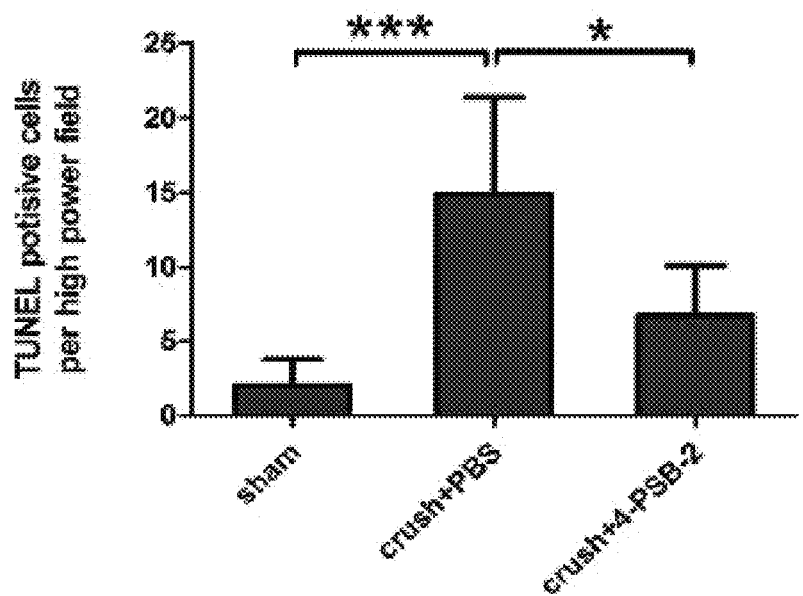

Figure 5
Figure 5A
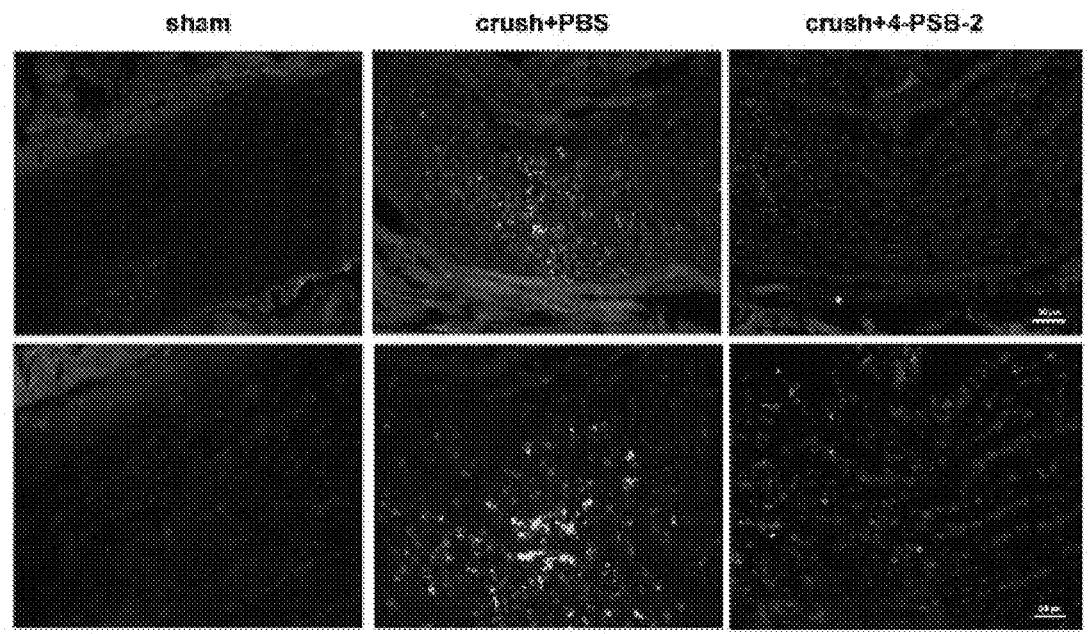
Figure 5B
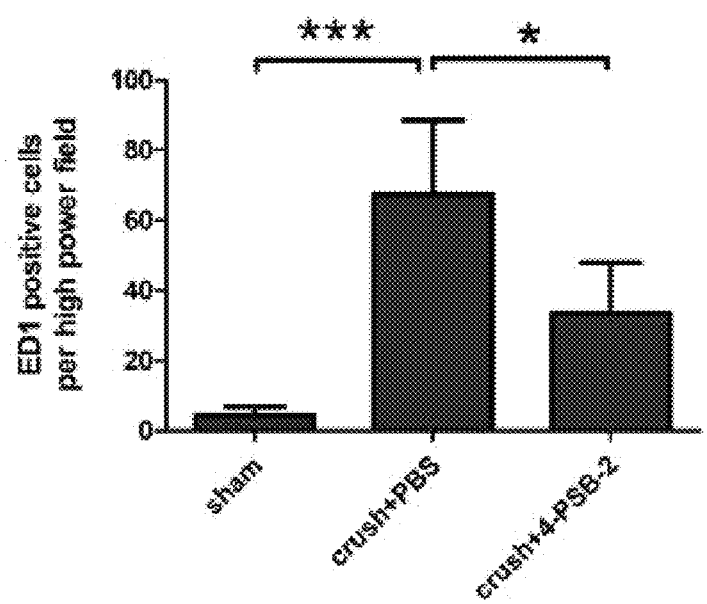

Figure 6
Figure 6A
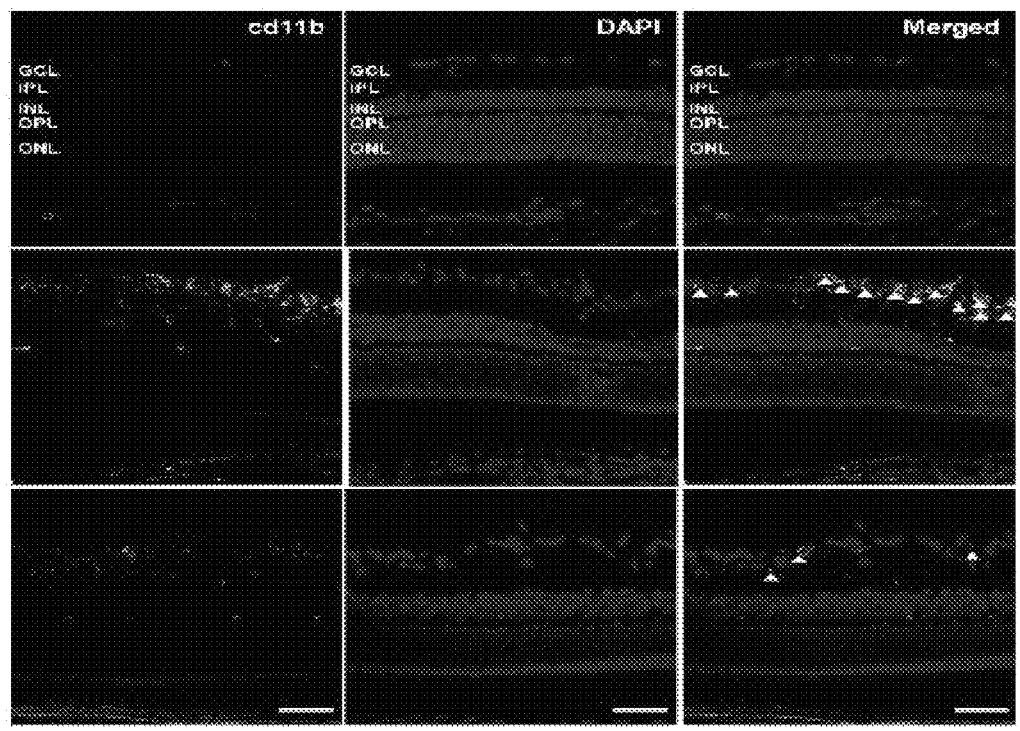
Figure 6B
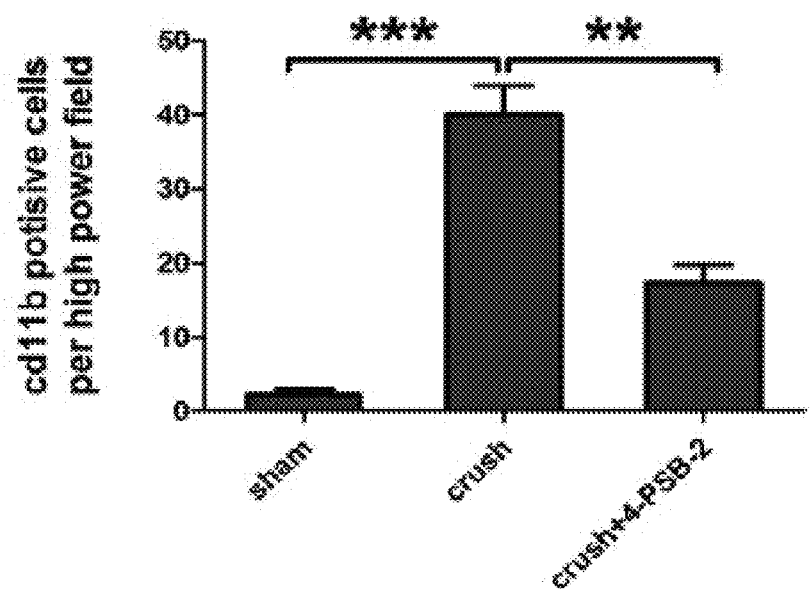

Figure 7
Figure 7A
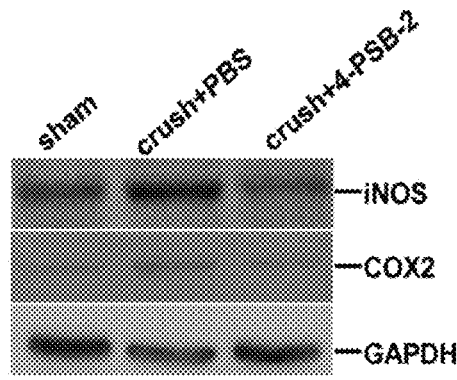
Figure 7B
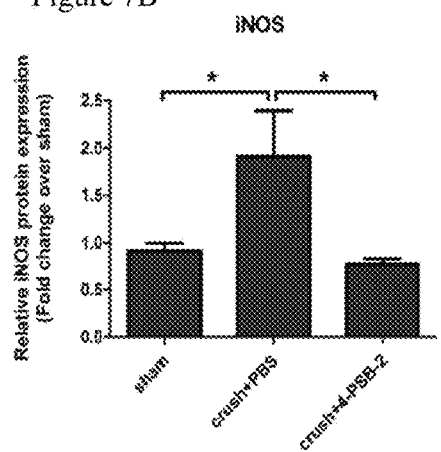
Figure 7C
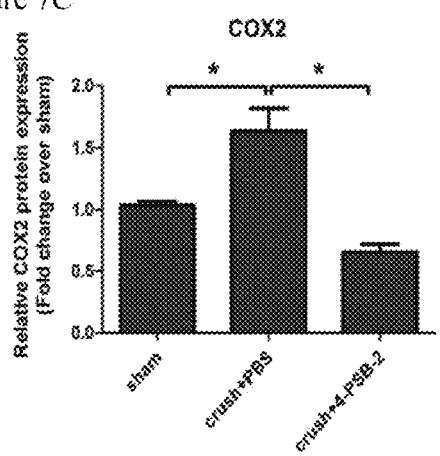
Figure 7D
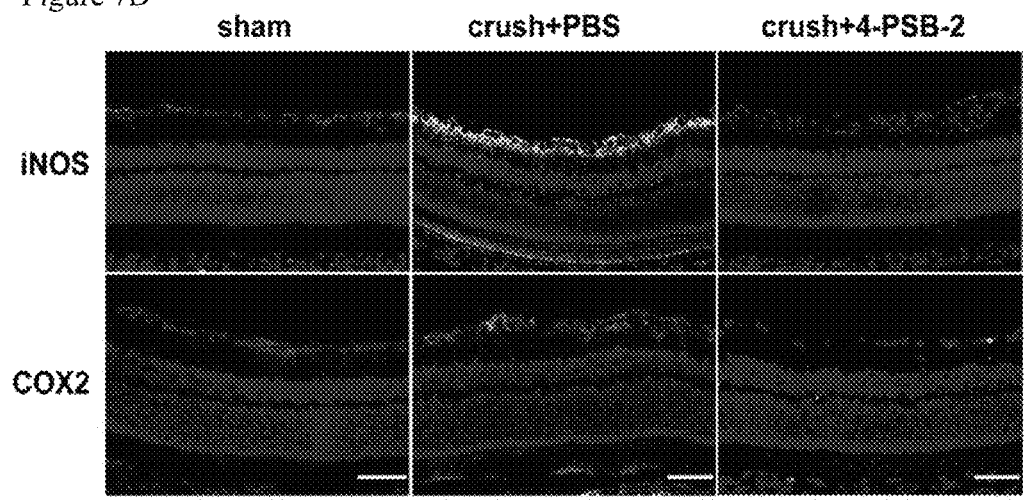

METHOD OF TREATING OR PREVENTING THE VISUAL FUNCTION LOSS BY USING 4-(PHENYLSULFANYL)BUTANE-2-ONE (4-PSB-2)

CROSS REFERENCE TO RELATED APPLICATIONS

The application claims the benefit of Taiwan application serial No. 105112654, filed on Apr. 22, 2016, and the subject matter of which is incorporated herein by reference.

FIELD OF THE INVENTION

The present disclosure generally relates to a compound 4-(phenylsulfanyl)butane-2-one (4-PSB-2) used to treat, prevent, and protect optic neuro visual function after crush injury.

BACKGROUND OF THE INVENTION

Traumatic optic neuropathy (TON) occurs in 0.5-5% of patients presenting with close head trauma and is often devastating cause of permanent visual loss. Damage to the optic nerve (ON) causes immediate shearing of and induces a vicious cycle of swelling and ischemia lead to RGCs and axon injury. In the majority of cases, the first critical event is RGC axonal damage, possibly mediated by glial dysfunction, following the apoptotic cell signaling, retrograde axonal degeneration and Wallerian degeneration. After ON transection, RGCs begin dying by apoptosis by first 3-7 days and the remainder (50-90%) have disappeared from the retina taking weeks to sometimes months. Axonal injury also induces a burst of superoxide within the RGC soma, following induction of downstream oxidative events and cytotoxic cytokines and results in apoptosis. Therefore, therapies that stimulate both neuronal viability and axon growth may prove beneficial after ON lesion.

The optic nerve crush model is an effective model for studying pathophysiology of RGCs death in axon injury and to evaluate the neuroprotective ability of several strategies for acute optic neuropathies. ON crush induces a retrograde degeneration of the RGCs after the injury. Prior to that, the myelin sheath of the axons degenerates, the ED-1 positive phagocytes (including macrophage and microglia) infiltrate and remove the myelin debris. Macrophage and microglia accumulation at the site of the insult contributes to glial scar formation in the ON, which is an obstacle for regeneration. These observations have implicated important roles of inflammatory processes in the ON crush injury. Inhibition of glial activation by both nitric oxide inhibitors and anti-inflammatory cytokines has been used to rescue RGC from apoptosis after axon injury.

In recent years, numerous marine invertebrates based compounds have been reported to show extensive anti-inflammatory activities, stimulation of neurogenesis, and modulation of receptors or voltage gated channels in central nervous system (CNS). Previous studies of bioactive marine natural products have led to isolation of several compounds with neuroprotective and anti-inflammatory activities from soft corals. Austrasulfone, a bioactive substance isolated from the Formosan soft coral *Cladiella australis*, exhibits potent neuroprotective effects. Dihydroaustrasulfone alcohol, the synthetic precursor of austrasulfone, not only exhibits anti-inflammatory activity in vitro, but also shows potent therapeutic potential in the treatment of inflammatory-related diseases.

However, the precursor has high polarity that reduces the ability of the precursor to pass through cell membrane. In light of this, the polar hydroxyl group (eOH) of hydroxylated sulfone was replaced with benzene ring in a straight-forward synthesis to yield the compound, 4-(Phenylsulfanyl) butane-2-one (4-PSB-2) in order to easily pass through the cell membrane.

SUMMARY OF THE INVENTION

The present invention relates to a method of protecting, treating or preventing the visual function loss in optic nerve in a subject after crush injury by using 4-(Phenylsulfanyl) butane-2-one (4-PSB-2). The pharmaceutically effective amount of 4-PSB-2 is 1-15 mg/kg body weight (BW). The present invention has the ability of enhancing the protection effect of RGCs, preserving the visual function in optic nerve after crush injury, recovering the visual function loss, attenuating apoptosis in optic nerve after injury, and inhibiting the inflammatory responses in optic nerves after ON injury.

BRIEF DESCRIPTION OF THE DRAWINGS

This patent or application file contains at least drawing executed in color. Copies of this patent or patent application publication with color drawing(s) will be provided by the Officer upon request and payment of the necessary fee.

The present disclosure will become more fully understood from the detailed description given hereinafter and the accompanying drawings which are given by way of illustration only, and thus are not limitative of the present disclosure, and wherein:

FIG. 1 shows the flat-mounted retina, FIG. 1A: the flat-mounted retina, wherein ON: optic nerve head, S: superior, I: inferior, N: nasal, and T: temporal; FIG. 1B: the distribution of FluoroGold labeling RGCs in the central retina, wherein ON: optic nerve head, and the white rectangular box indicates the area for RGC counting: 38,250 $mm^2$ (225×170 mm).

FIG. 2A-FIG. 2F are representative flat preparation of central and mid-peripheral retinas; FIG. 2A and FIG. 2D: sham operation; FIG. 2B and FIG. 2E: crush and PBS-treated retinas; FIG. 2C and FIG. 2F: crush and 4-PSB-2-treated retinas; FIG. 2G and FIG. 2H: morphometry of RGCs in the central and mid-peripheral retinas. RGC densities of central and mid-peripheral retinas in the sham group were 2359±423/$mm^2$ and 1400±242/$mm^2$, respectively. Two weeks after ON crush, the densities of RGCs in the central retina of the 4-PSB-2-treated group and PBS-treated group were 1342±473/$mm^2$ (56.8% survival) and 500±116/$mm^2$ (21.1% survival) respectively, and in mid-peripheral retina were 915±244/$mm^2$ (65.3% survival) and 420±155/$mm^2$ (30.0% survival) respectively (n=6 in each group) *p<0.05.

FIG. 3 shows flash VEPs result; FIG. 3A: representative flash VEP tracings at 2 weeks after ON crush; FIG. 3B: the latency of the P1 wave was 83±3 ms, 154±23 ms and 118±14 ms in the sham, PBS-treated and 4-PSB-2-treated rats, respectively (p<0.05 vs PBS-treated rats; p<0.001 vs sham group, n=6 in each group, *p<0.05).

FIG. 4 shows TUNEL assay result in retinal sections. FIG. 4A: reprehensive of the TUNEL in the retinas among the three groups; FIG. 4B: illustrates that there were 2.0±1.7 positive cells/HPF in the RGC layers of retina in the sham-operated rats, 14.8±6.5 positive cells/HPF in the PBS-treated group and 6.7±3.4 positive cells/HPG in the 4-PSB-2-treated rats (p<0.05 vs. PBS-treated group and p<0.05 vs. sham group), n=6 in each group, *p<0.05, ***p<0.001, scale bar: 50 μM.

FIG. 5 shows immunohistochemistry result of ED1 in ONs at 2 weeks after ON crush; FIG. 5A: representative of ED1 staining in the longitudinal sections of ON; FIG. 5B: indicates that the ED1 positive cells/HPF in the sham group, PBS-treated group and 4-PSB-2-treated group were 4.3±2.5, 67.3±21.1 and 33.5±14.5, respectively (p<0.05 vs. PBS treated group and p<0.05 vs. sham group), n=6 in each group, *p<0.05, ***p<0.001.

FIG. 6 shows immunohistochemistry result of Cd11b in the retinas at 2 weeks after ON crush; FIG. 6A: representative of Cd11b staining (arrowhead) in the retina sections; FIG. 6B: indicates that the Cd11b positive cells/HPF in the sham group, PBS-treated group and 4-PSB-2-treated group were 2.3±1.7, 40.0±9.7 and 17.3±5.9, respectively (p<0.01 vs. PBS-treated group and p<0.05 vs. sham group), n=6 in each group, p<0.01, *p<0.001, scale bar: 20 μM.

FIG. 7 shows immunoblotting and immunohistochemical analysis results of expression level of iNOS and COX-2 in the retinas after ON crush; FIG. 7A: effects of 4-PSB-2 on suppression of iNOS and COX-2 in the retina at 2 weeks after ON crush; FIG. 7B and FIG. 7C: quantitative analysis of FIG. 7A, in the bar graph, the expression level of iNOS and COX-2 are expressed as a ratio to GAPDH expression, values for sham-operated retinas were set to 1, results represent the means±S.D for three independent experiments, *p<0.05; FIG. 7D: immunohistochemical analysis of ON crush-induced retina iNOS and COX-2 expression with or without 4-PSB-2 treatment, scale bar: 50 μM.

Figure 2:
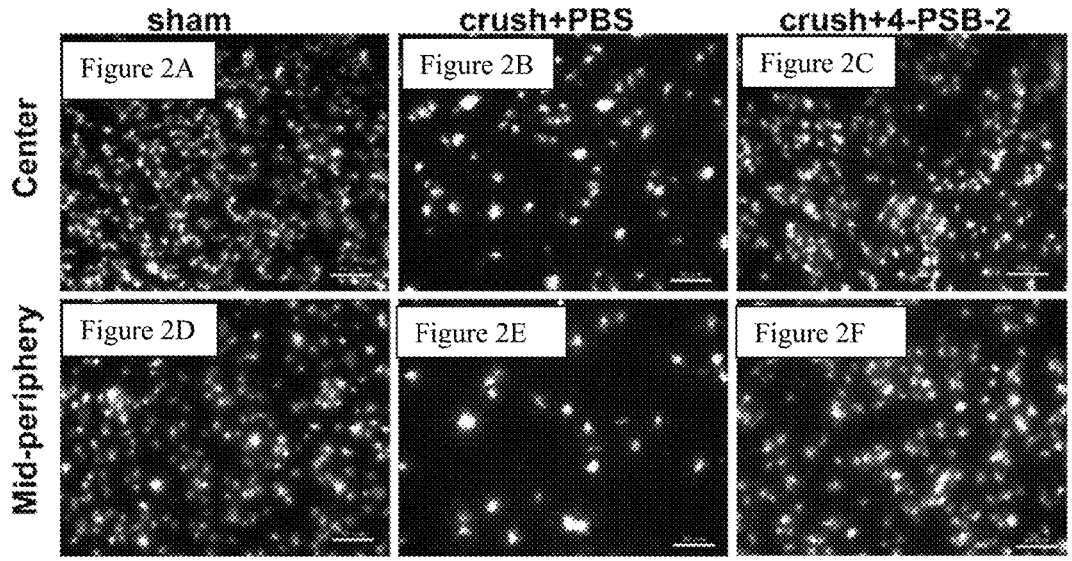
FIG. 2 shows the flat mount preparations of retinas and morphometry of RGCs at 2 weeks after retrograde Fluoro-Gold labeling.
Figure 2:
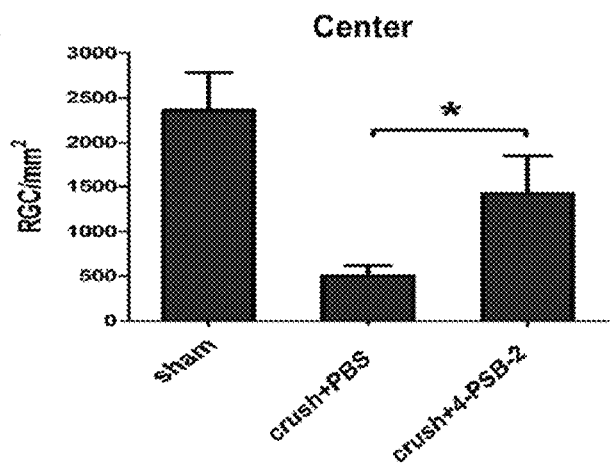
Figure 2:
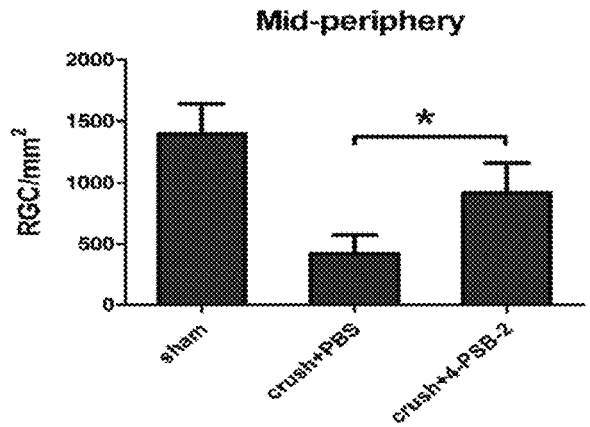

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the disclosure.

DETAILED DESCRIPTION OF THE INVENTION

The present invention provides a method of treating the visual function in optic nerve after crush injury by using a pharmaceutical composition comprising 4-(Phenylsulfanyl) butane-2-one (4-PSB-2) and pharmaceutically acceptable carrier, wherein the 4-PSB-2 comprises formula I. The optic nerve is retinal ganglion cells (RGCs).

The pharmaceutically effective amount of 4-PSB-2 is 1-15 mg/kg body weight (BW). Preferably the dose is 5-15 mg/kg body weight (BW). Preferably the dose is 5 mg/kg body weight (BW).

4-PSB-2 has a neuroprotective effect on ON as well as in RGCs after ON crush in a subject. The RGCs start apoptosis once the optic nerve being hurt, and this is one of the reason the vision loses. 4-PSB-2 may work by being anti-apoptotic and by attenuation of the inflammatory responses involving less ED1 (biomarker of macrophage and microglia) positive cells infiltration in ON as well as suppression of iNOS/COX-2 signaling pathway in the retinas to rescue RGCs after ON crush injury.

Furthermore, the visual function as demonstrated by flash visual evoked potential test (FVEP) was also better preserved in the 4-PSB-2-treated eyes compared to the vehicle-treated ones, confirming the beneficial effect on the ocular structures. 4-PSB-2 also has the ability to recover the vision after ON crush. 4-PSB-2 can reduce the loss of nerve conduction which is caused by optic nerve damage, and therefore preserve the visual function after ON crush injury.

Previous study shows an important role of iNOS and COX-2 in the pathogenesis of RGC loss after crush injury. NO production from iNOS contributes to cytotoxicity resulting in neuron death and axonal damage. COX-2 signaling has also been shown to involve in the apoptotic death of neurons. Numerous bioactive compounds derived from coral exhibit neuroprotective qualities via anti-inflammatory pathways, such as reduction of iNOS and COX, to halt apoptosis of the neuron cells. Administration of 4-PSB-2 is anti-apoptotic on RGCs after ON crush injury. The present invention also demonstrates that 4-PSB-2 significantly reduced expression of iNOS and COX-2 in the ON crushed-retina. Hence, 4-PSB-2 can be anti-apoptotic by this mechanism.

ON injury is associated with local inflammatory processes at the site of injury. After ON crush, ED-1-labeled macrophage/microglia accumulated at the site of injury. Furthermore, activation of microglia and excessive amounts of pro-inflammatory mediators release by microglia has been observed during the pathogenesis of neuronal death in CNS injury. It has been reported that multiple inflammatory mediators, such as TNF-α, IL-6, MCP-1, iNOS, and COX-2, are upregulated and implicated in the pathogenesis of ON crush injury. Several investigations have found that nerve injury can initiate iNOS and COX-2 expression in macrophage/microglia at the injury site.

Elevated level of iNOS and COX-2 released by activated inflammatory cells, glial elements, and injured neurons, are consistent with an acute inflammatory process in ON crush injury. ED-1 positive macrophage/microglia accumulated remarkably at the ON lesion site; Cd11b-labeled microglia predominantly enhanced in the RGC layers. Immediate administration of 4-PSB-2 attenuated the accumulation of ED-1 positive macrophage/microglia at the ON lesion site, and suppressed the expression of Cd11b, iNOS and COX-2 in the retina after crush injury.

In one embodiment, Cd11b-labeled microglia predominantly enhanced in the RGC layers and the level of pro-inflammatory markers, iNOS and COX2, were significantly elevated in the retina after crush insult. Immediate administration of 4-PSB-2 attenuated the accumulation of ED-1 positive macrophage/microglia at the ON lesion site, and suppressed the expression of Cd11b, iNOS and COX-2 in the retina after crush injury. 4-PSB-2 exhibits anti-inflammatory activities through the suppression of iNOS and COX2 signaling in the retina after ON injury, hence exhibits the neuro protective effect.

Therefore, the present invention provides a compound for preparing a pharmaceutical composition in treating optic nerve injury, wherein the compound is 4-PSB-2. 4-PSB-2 can preserve/recover visual function after optic nerve crush injury by its anti-apoptotic and anti-inflammatory ability to contribute to RGC survival.

In an embodiment, the pharmaceutical composition of present invention can be oral medication, injection drug, or eye drops.

In an embodiment, the pharmaceutical composition of present invention can be given by injection, oral administration, eye drop, or spray.

In an embodiment, the pharmaceutical composition of present invention can be powder, tablet, capsule, or liquid, or any pharmaceutically acceptable forms.

The "subject" as used herein is an animal, especially a mammal.

In a prefer embodiment, the subject is human.

The term "effective dose" as used herein refers to an amount of a pharmaceutical composition of the invention, alone or in combination with another drug that provides a therapeutic benefit in the treatment of the symptoms. The term "mg/kg body weight (mg/kg)" is used to indicates the dose (in milligrams) corresponding to the body weight of the subject (kg).

EXAMPLES

Materials and Methods
Animal Model

Forty five adult male Wistar rats weighing 150-180 g (7-8 weeks old) were used and grouped (Table 1). All manipulations were performed with animals under general anesthesia induced by an intramuscular injection of a mixture of ketamine (40 mg/kg body weight (BW)) and xylazine (4 mg/kg BW). In addition, topical 0.5% Alcaine eye drops (Alcon, Puurs, Belgium) were used to perform topical anesthesia. The rats had free access to food and water, and were maintained in an environmentally controlled room that was held at a temperature of 23±1° C., a humidity of 55±5% and had a 12 h light-dark cycle (light period: 7 AM to 7 PM).

TABLE 1

| Method | Group | Number of rats |
|---|---|---|
| FVEP, TUNEL, IHC | Sham | 6 |
|  | Crush + PBS | 6 |
|  | Crush + 4-PBS-2 | 6 |
| FG retrograde labeling | Sham | 6 |
|  | Crush + PBS | 6 |
|  | Crush + 4-PBS-2 | 6 |
| Immunoblotting analysis | Sham | 3 |
|  | Crush + PBS | 3 |
|  | Crush + 4-PBS-2 | 3 |

Preparation of 4-(phenylsulfanyl)butan-2-one (4-PSB-2)

The bezenethiol (2.0 g, 98%, 17.8 mmole) and triethylamine (0.25 mL, 1.78 mmole) were added in a round bottom flask containing 10 mL of acetone. Followed by stirring at 0° C., a solution of methyl vinyl ketone (1.38 mL, 90%, 17.8 mmol) in 4 mL of acetone was slowly added into the mixture. The temperature of the mixture was raised to room temperature and the reaction was continued for 16 h. The solvent free product was subject to silica gel column chromatography, eluting with n-hexane/ethyl acetate (25:1), to afford 4-(phenylsulfanyl)butan-2-one (2.80 g, yield 87%). The reaction was shown as followed:

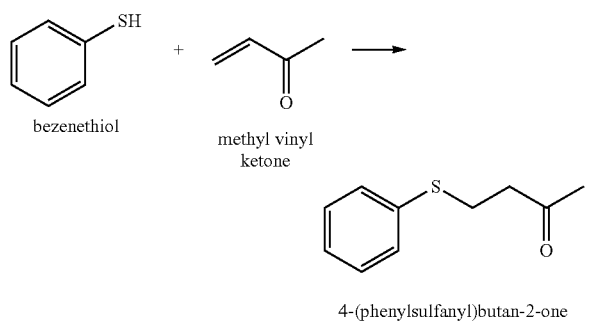

Optic Nerve Crush Injury Experiment

After general anesthesia and topical Alcaine eye drop application, the ON was exposed and isolated. Care was taken to avoid damaging the small vessels around the ON. A vascular clip (60 g micro-vascular clip) was then applied to the ON 2 mm posterior to the globe for 30 seconds. After the surgery, Tobradex eye ointment (Alcon, Puurs, Belgium) was administered. The rats were kept on electric heating pads at 37° C. for recovery. The control group received a sham operation that entailed ON exposure without the crush. 4-PSB-2 (5 mg/kg in 0.2 mL phosphate-buffered saline) or phosphate buffered saline (PBS control) was immediately administered after ON crush once by subcutaneous injection.

Flash Visual-Evoked Potentials (FVEPs)

For the functional evaluation of the ON, FVEPs were recorded 2 weeks after ON crush in 18 experimental rats. An isolated silver plate electrode was placed extradurally through a 2-mm diameter craniotomy over the visual cortex using the stereotactic coordinates (bregma −8 mm, lateral 3 mm) and a modified method described by Ohlsson et al. A visual electro-diagnostic system (UTAS-E3000, LKC Technologies, Gaithersburg, Md., USA) was used to measure FVEPs. After 10 min of light adaptation, photopic FVEP was performed, based on the report showing no significant differences of latency between photopic and scotopic VEP in Wistar rats. The settings were: background illumination off, a flash intensity of Ganzfeld 0 db, single flash with flash rate on 1.9 Hz, the test average at 80 sweeps, the threshold for rejecting artifacts at 50 mV and a sample rate of 2000 Hz. The latency of the first positive wave (P1) of the FVEP among groups was compared (n=6 in each group).

Retrograde Labeling of RGCs with Fluoro-Gold (FG) and Densities of RGCs

In order to evaluate the neuroprotective effect of 4-PSB-2 in the RGCs, the retrograde labeling of RGC was performed by injection of fluoro-gold (FG) in the superior colliculus (SC). With this technique, only the RGCs with intact axons projected to the SC were labeled with FG. The procedure was performed based on Chang et al (Exp. Eye Res., 2004, 118, 109-116). Briefly, one week before sacrificing, the rats were anesthetized using a ketamine (100 mg/kg) and Xylazine (10 mg/kg) mixture, and then placed in a stereotactic apparatus. An amount of 1.5 ml of 5% of FG (Fluorochrome, Denver, Colo., USA) was injected into the superior colliculus on each side. One week after labeling, the eyeballs were harvested after euthanasia of the animals. The eyeballs were placed in 10% formalin and iii the whole retina was then carefully dissected, flattened. The retina was examined with a 400× epi-fluorescence microscope equipped with a filter set (excitation filter=350-400 nm; barrier filter=515 nm), as well as a digital camera and software. The retinas were examined for RGCs at a distance of 1 or 3 mm from the optic nerve head in order to provide the central and mid-peripheral RGC densities respectively (FIG. 1A). RGCs were counted in eight areas randomly of 38,250 mm² (225×170 mm)/each in the central (about 40% of the central area) (FIG. 1B), and eight areas randomly of 38,250 mm²/each in the mid-peripheral (about 30% of the mid-periphery) regions of each retina. The averages of these areas were taken as the mean density of RGCs per retina. RGC survival percentage was defined as the number of RGCs in each treatment group divided by the number of RGCs in the sham operated retina, multiplied by 100.

Optic Nerves and Retina Section Preparation

Segments of the ON (5-7 mm long) between the optic chiasm and the eyeball were harvested upon sacrifice at two weeks after the experiments. The nerves were immediately frozen at −70° C. for future immunohistochemical studies. After sacrifice, the corneas, lenses and vitreous bodies were removed. The remaining eyecups containing sclera and retinas were fixed in 4% paraformaldehyde for 2 hours at room temperature. The tissues were then dehydrated in 30% sucrose overnight and kept at −20° C. until further processing could be performed for sectioning.

TUNEL Assay

To ensure the use of equivalent fields for comparison, all retinal frozen sections were prepared with retinas at 1-2 mm distance from the optic nerve head. TUNEL reactions (Dead-End™ fluorometric TUNEL System, Promega Corporation, Madison, Wis., USA) were performed to detect apoptotic cell. The TUNEL positive cells in the RGC layer of each sample were counted in ten high powered fields (HPF, ×400 magnification), and three sections per eye were averaged.

Immunohistochemistry (IHC) in the ONs and Retina

IHC of ED1 (CD68, a marker of macrophage/microglia) in the ONs and IHC of CD11b, iNOS and COX-2 in the retina using monoclonal antibodies (ED1, 1:50; CD11b, 1:20; AbD Serotec, Oxford, UK) or polyclonal antibodies (iNOS, 1:50; Cell signaling Inc. Beverly, Mass., USA; COX-2, 1:50; Santa Cruz, Calif., USA) were performed. The frozen ON and retina sections were fixed with acetone at −20° C. for 30 min and blocked with 5% fetal bovine serum (FBS) containing 1% bovine serum albumin (BSA) for 15 min. The primary antibody was applied and incubated overnight at 4° C. The secondary antibody conjugated with fluorescein isothiocyanate (FITC, 1:100) was applied at room temperature for 1 hour. Counterstaining was performed using DAPI. For comparison, ED1 positive cells were counted in six HPF at the lesion site of ON (six rats in each group). Cd11b positive cells were counted in six HPF and three sections per eye were averaged.

Immunoblot Analysis

Total retinal protein was extracted from homogenized samples using modified radioimmunoprecipitation (RIPA) buffer with a Halt™ protease and phosphatase inhibitor cocktail (Thermo Scientific, Rockford, USA). Protein concentrations were determined using the Protein Assay kit. Each retina was served as an individual sample (n=3 in each group). Protein samples containing 50 mg of protein were separated on 12% sodium dodecyl sulphate-polyacrylamide gels and transferred to polyvinylidene difluoride (PVDF) membranes. The membranes were incubated in TBST buffer supplemented with 5% dry skim milk for 30 min to block nonspecific binding. iNOS and COX-2 antibodies were added and the preparations were incubated at 4° C. overnight. After washing, the blots were incubated in the appropriate anti-horseradish peroxidase-conjugated secondary antibody at room temperature for 1 h. The proteins on the membranes were detected using an enhanced chemiluminescence (ECL) system. The blots were also probed with an antibody for glyceraldehyde-3-phosphate dehydrogenase (GAPDH) as an internal loading control. Densitometric analysis was conducted using ImageJ software. Each experiment was repeated three times with independent retinal samples from different animals. For comparison, the ratio of iNOS or COX-2 signaling/GAPDH signaling on sham-operated retina was regarded as 1.0 fold.

Statistical Analysis

All measurements were performed in a masked fashion. Statistical analysis was performed with commercial software (IBM SPSS Statistics 19, International Business Machine Corp., Armonk, N.Y.). The KruskaleWallis test and ManneWhitney U test were used for comparisons between each group. Data are presented as the means±standard deviation (S.D). In all cases, a value of $p<0.05$ was considered statistically significant.

Result

Morphometry of RGCs

The densities of RGCs in the central and mid-peripheral retina in the sham-operated eyes were $2359\pm423/mm^2$ and $1400\pm242/mm^2$, respectively. Two weeks after ON crush, the densities of RGCs in the central retina of the 4-PSB-2-treated group and PBS-treated group were $1342\pm473/mm^2$ (56.8% survival) and $500\pm116/mm^2$ (21.1% survival) respectively, and in mid-peripheral retina were $915\pm244/mm^2$ (65.3% survival) and $420\pm155/mm^2$ (30.0% survival) respectively (FIG. 2). The results demonstrated that RGC survival rate increased by approximately 35.7% in the central retina and 35.3% in the mid-peripheral retina in the 4-PSB-2-treated group as compared to the PBS-treated group ($p<0.05$). Therefore, the result indicated and supported that 4-PSB-2 of the present invention has significant neuro protective effect, and can recover the visual function after optic neuro injury.

FVEP

The latency of the P1 wave at the 2 week after ON crush was 83±3 ms, 154±23 ms and 118±14 ms in the sham, PBS-treated and 4-PSB-2-treated rats, respectively ($p<0.05$ vs PBS-treated rats; $p<0.001$ vs sham group) (FIG. 3). The FVEP results demonstrated that the 4-PSB-2-treated group had significantly preserved visual function as compared to the PBS-treated group at 2 weeks after ON crush.

TUNEL Assay

TUNEL assay demonstrated that TUNEL positive cells/HPF (high powered field) was 2.0±1.7 cells in the sham-operated rats, 14.8±6.5 positive cells/HPF in the PBS-treated group and 6.7±3.4 positive cells/HPG in the 4-PSB-2-treated rats ($p<0.05$ vs. PBS treated group and $p<0.05$ vs. sham group) in the RGC layer (FIG. 4). The results demonstrated that administration of 4-PSB-2 had a significant anti-apoptotic effect on RGCs after ON crush.

ED1 in the ON

At two weeks after ON crush insult, the ED1 positive cells/HPF in the sham group, PBS-treated group and 4-PSB-2-treated group were 4.3±2.5, 67.3±21.1 and 33.5±14.5, respectively ($p<0.05$ vs. PBS-treated group and $p<0.05$ vs. sham group) (FIG. 5). These results indicated that 4-PSB-2 administration had anti-inflammatory effects at the ON after insult, as demonstrated by less ED-1 labeled macrophage/microglial accumulation at ONs.

CD11b in the Retina

The upregulation of Cd11b, the beta-integrin marker of microglia, represents microglial activation during neurodegenerative inflammation. At two weeks after ON crush insult, the number of Cd11b positive cells, representing activated microglia, prominently increased in the ganglion cell layer in the PBS-treated retina (FIG. 6). The Cd11b positive cells/HPF in the sham group, PBS-treated group and 4-PSB-2-treated group were 2.3±1.7, 40.0±9.7 and 17.3±5.9, respectively ($p<0.01$ vs. PBS-treated group and $p<0.05$ vs. sham group). These results indicated that 4-PSB-2 administration had anti-inflammatory effects in the retina after insult, as demonstrated by less Cd11b-labeled microglial activation in the retina.

Suppression of iNOS, and COX-2 Expression by 4-PSB-2

The expression level of iNOS and COX-2 (FIG. 7A-7C) was significantly elevated in the PBS-treated retinas at two weeks after ON crush. 4-PSB-2 treatment prevented the increase in iNOS and COX-2 expression induced by optic nerve injury. The enhanced immunoreactivity of iNOS and COX-2 was observed in the RGC layers in the PBS-treated retinas compared with the 4-PSB-2 treated and sham retinas (FIG. 7D). These results indicated that 4-PSB-2 attenuates the elevated pro-inflammatory cytokines, iNOS and COX-2 expression in the retina after ON crush injury.

As used herein, the terms "comprises," "comprising," "includes," "including," "has," "having" or any other variation thereof, are intended to cover a non-exclusive inclusion. Unless expressly stated to the contrary, "or" refers to an inclusive or and not to an exclusive or As used herein, the singular forms "a", "an" and "the" include plural reference unless the context clearly dictates otherwise.

As used herein, the term "inhibit", "decrease", "prevent", or any variation thereof, when applied in the claims and/or specification includes any measurable reduction or complete inhibition to reach a desired result.

As used herein, the term "effective" in the claims and/or specification is intended to be sufficient to achieve the desired or expect results.

Those skilled people in the art would realize that the present invention can be readily ascertained to attaining the objects and advantages mentioned in the present invention, as well as those existing therein. The cells, animals and procedures and methods in the present invention are representative of preferred embodiments and are exemplary and not limited to the field of the invention. Those skilled in the art will recognize modifications and other uses therein. Such modifications are intended to be included within the spirit of the invention and defined in the appended iii claims.

What is claimed is:

1. A method of treating the visual function loss in optic nerve in a subject after optic nerve crush injury, comprising administering a pharmaceutical composition to the subject, wherein the composition comprises 4-(Phenylsulfanyl)butane-2-one (4-PSB-2), and pharmaceutically acceptable carrier, wherein the 4-PSB-2 comprises formula I

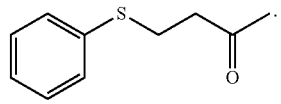

(formula I)

2. The method according to claim 1, wherein the optic nerve is retinal ganglion cells (RGCs).

3. The method according to claim 1, wherein the pharmaceutically effective amount of 4-PSB-2 is 1-15 mg/kg body weight (BW).

4. The method according to claim 1, wherein the pharmaceutically effective amount of 4-PSB-2 is 5 mg/kg body weight (BW).

5. The method according to claim 1, wherein the 4-PSB-2 has the ability of inhibiting optic nerve inflammation.

6. The method according to claim 1, wherein the 4-PSB-2 has the ability of inhibiting optic nerve cell apoptosis.

7. The method according to claim 1, wherein the pharmaceutical composition is powder, tablet, capsule, or liquid, or any pharmaceutically acceptable forms.

8. The method according to claim 1, wherein the subject is mammal.

* * * * *